(12) United States Patent
Emil et al.

(10) Patent No.: US 11,660,134 B2
(45) Date of Patent: May 30, 2023

(54) INSTRUMENTS AND METHODS FOR DELIVERING BONE CEMENT TO A BONE SCREW

(71) Applicant: Medos International Sarl, Le Locle (CH)

(72) Inventors: Cory Emil, Milton, MA (US); Richard W. Fournier, New Bedford, MA (US); Eric Biester, Barrington, RI (US); Ellen E. Wasserbauer, Mendon, MA (US)

(73) Assignee: Medos International Sarl, Le Locle (CH)

( * ) Notice: Subject to any disclaimer, the term of this patent is extended or adjusted under 35 U.S.C. 154(b) by 518 days.

(21) Appl. No.: 16/439,977

(22) Filed: Jun. 13, 2019

(65) Prior Publication Data

US 2020/0390484 A1 Dec. 17, 2020

(51) Int. Cl.
*A61B 17/88* (2006.01)
*A61B 17/86* (2006.01)
(52) U.S. Cl.
CPC ........ *A61B 17/8816* (2013.01); *A61B 17/864* (2013.01); *A61B 17/8811* (2013.01)
(58) Field of Classification Search
CPC ...................................... A61B 17/88–17/8847
See application file for complete search history.

(56) References Cited

U.S. PATENT DOCUMENTS

| | | | |
|---|---|---|---|
| 6,565,572 B2 | 5/2003 | Chappius | |
| 7,097,648 B1 | 8/2006 | Globerman et al. | |
| 7,354,442 B2* | 4/2008 | Sasso | A61B 17/8615 606/280 |
| 7,749,225 B2 | 7/2010 | Chappuis et al. | |
| 8,211,156 B2 | 7/2012 | Andersen et al. | |
| 8,303,598 B2 | 11/2012 | Frankel et al. | |
| 8,360,629 B2 | 1/2013 | Globerman et al. | |
| 8,415,407 B2 | 4/2013 | Beyar et al. | |
| 8,690,883 B2 | 4/2014 | Collins et al. | |
| 8,747,411 B2 | 6/2014 | Mitchell | |

(Continued)

FOREIGN PATENT DOCUMENTS

CN 109276303 A 1/2019

OTHER PUBLICATIONS

U.S. Appl. No. 16/440,602, dated Jun. 13, 2019 (54 pages).

(Continued)

*Primary Examiner* — Zade Coley
(74) *Attorney, Agent, or Firm* — Mintz Levin Cohn Ferris Glovsky and Popeo, P.C.

(57) ABSTRACT

Instruments and methods for delivering bone cement are disclosed herein. In one exemplary embodiment, the instrument includes a cannulated bone screw having a head that is configured to be received within a rod receiver and a shank extending distally from the head and configured to extend distally from the rod receiver, a cannulated shaft having a distal end configured to extend into the shank of the cannulated bone screw and a proximal end configured to couple to a bone cement delivery system, and a retaining sleeve disposed around at least a portion of the cannulated shaft. The head of the bone screw has proximal and distal recesses therein, and a distal end of the retaining sleeve is configured to couple to the proximal recess.

20 Claims, 9 Drawing Sheets

(56) References Cited

U.S. PATENT DOCUMENTS

| | | |
|---|---|---|
| 8,821,506 B2 | 9/2014 | Mitchell |
| 9,326,801 B2 | 5/2016 | Poulos |
| 9,333,018 B2 * | 5/2016 | Russell ................. A61B 17/80 |
| 9,381,024 B2 | 7/2016 | Globerman et al. |
| 9,480,518 B2 | 11/2016 | Biedermann et al. |
| 9,504,505 B2 * | 11/2016 | Giancola ............ A61B 17/7098 |
| 9,549,760 B2 | 1/2017 | Steele |
| 9,668,798 B2 * | 6/2017 | Giersch ............. A61B 17/8605 |
| 9,730,745 B2 | 8/2017 | Biedermann et al. |
| 9,993,276 B2 * | 6/2018 | Russell ............. A61B 17/7098 |
| 2004/0225292 A1 * | 11/2004 | Sasso ................ A61B 17/8816 |
| | | 606/916 |
| 2006/0264967 A1 | 11/2006 | Ferreyro et al. |
| 2007/0032567 A1 | 2/2007 | Beyar et al. |
| 2008/0228192 A1 | 9/2008 | Beyar et al. |
| 2009/0138043 A1 | 5/2009 | Kohm |
| 2009/0264895 A1 | 10/2009 | Gasperut et al. |
| 2009/0287218 A1 | 11/2009 | Beger et al. |
| 2010/0004656 A1 | 1/2010 | Marins Dos Reis, Jr. |
| 2010/0114174 A1 * | 5/2010 | Jones ................ A61B 17/8816 |
| | | 606/279 |
| 2010/0256688 A1 * | 10/2010 | Giersch ................. A61B 17/68 |
| | | 606/305 |
| 2011/0040337 A1 | 2/2011 | Budassi |
| 2011/0098714 A1 | 4/2011 | Her et al. |
| 2012/0046698 A1 | 2/2012 | Kolb et al. |
| 2013/0253595 A1 | 9/2013 | Zucherman et al. |
| 2014/0163566 A1 | 6/2014 | Phan et al. |
| 2015/0073423 A1 | 3/2015 | Hoefer et al. |
| 2015/0173818 A1 | 6/2015 | Baroud et al. |
| 2015/0272646 A1 * | 10/2015 | Russell .............. A61B 17/8695 |
| | | 606/304 |
| 2015/0374417 A1 | 12/2015 | Petit et al. |
| 2016/0000478 A1 | 1/2016 | Fischer et al. |
| 2016/0213413 A1 * | 7/2016 | Hientzsch ............ A61B 17/864 |
| 2018/0014862 A1 | 1/2018 | Raina et al. |
| 2018/0368893 A1 | 12/2018 | Divincenzo et al. |

OTHER PUBLICATIONS

U.S. Appl. No. 16/440,618, dated Jun. 13, 2019 (52 pages).
International Search Report and Written Opinion for International Application No. PCT/EP2020/065379, dated Oct. 15, 2020, 16 pages.

* cited by examiner

INSTRUMENTS AND METHODS FOR DELIVERING BONE CEMENT TO A BONE SCREW

FIELD

Instruments and methods are provided for delivering bone cement to a bone screw.

BACKGROUND

Bone screws, such as pedicle screws, can be used in orthopedic surgery to fix bone during healing, fusion, or other processes. In spinal surgery, for example, bone screws can be used to secure a spinal fixation element to one or more vertebrae to rigidly or dynamically stabilize the spine.

In many instances, particularly in spinal surgeries, the patient may have diminished or osteoporotic bone quality, which lessens the purchase of bone screws in such bone structure. As a result, this can preclude stabilization of the vertebrae and can lead to bone screw loosening and pullout. To improve bone screw fixation, bone cement can be introduced into bone proximate to the bone screw.

Bone screw augmentation typically uses cannulated/fenestrated bone screws for injecting bone cement into the bone structure having the fenestrated bone screw therein. For example, once a cannulated/fenestrated bone screw is inserted into bone, a cannula and/or guide can be docked to the head assembly. The docked cannula and/or guide functions as an alignment guide to the shank of the bone screw and allows access to the shank's fenestration(s). As such, cement delivery is effected by inserting a cement delivery shaft through the docked cannula and/or guide and into the shank of the bone screw, and pumping bone cement through the shaft and into the shank of the bone screw. In use, however, coupling of the cannula and/or guide to the head assembly and securing proper alignment of the cannula and/or guide with the shank can be challenging, particularly where direct visualization of the bone screw is compromised. Clinically, this can hinder intraoperative stability, interfere with the procedural workflow, and increase the number of surgical steps. Moreover, since the cannula and/or guide functions as an alignment guide for cement delivery, insufficient coupling to the head assembly and/or misalignment with the shank of the bone screw can result in cement leakage or failure of the cement delivery shaft.

Accordingly, there remains a need for improved instrumentation and methods associated with delivering bone cement to a bone screw.

SUMMARY

Various instruments and methods are disclosed for delivering bone cement to a bone screw.

In one embodiment, an instrument is provided and includes a cannulated bone screw, a cannulated shaft and a retaining sleeve disposed around at least a portion of the cannulated shaft. The cannulated bone screw has a head that is configured to be received within a rod receiver, and a shank extending distally from the head and configured to extend distally from the rod receiver. The head has proximal and distal recesses therein. The cannulated shaft has a distal end that is configured to extend into the shank of the cannulated bone screw, and a proximal end that is configured to couple to a bone cement delivery system. The retaining sleeve has a distal end that is configured to couple to the proximal recess in the head of the bone screw.

In some embodiments, the instrument can include a coupling assembly that is configured to selectively couple the cannulated shaft to the retaining sleeve to prevent axial translation of the cannulated shaft relative to the retaining sleeve.

The coupling assembly can have a variety of configurations. In some embodiments, the coupling assembly can be coupled to the proximal end of the retaining sleeve. For example, a distal end of the coupling assembly can be threadably coupled to the proximal end of the retaining sleeve.

In some embodiments, the coupling assembly can include a release mechanism that can be configured to selectively disengage the cannulated shaft from the retaining sleeve. The release mechanism can have a channel extending therethrough, in which the channel can at least partially overlap with a lumen that extends through an annular body such that the coupling assembly can be disposed around a portion of the cannulated shaft. The coupling assembly can also include a biasing element that can bias the release mechanism toward a groove of the cannulated shaft.

The cannulated bone screw can have a variety of configurations. In some embodiments, the proximal recess of the cannulated bone screw can be threaded, and the distal end of the retaining sleeve can be threadably coupled to the threaded proximal recess.

In another exemplary embodiment, an instrument is provided having a cannulated bone screw, a cannulated shaft, and a guiding assembly that is partially disposed around the cannulated shaft. The cannulated bone screw has a head that is configured to couple to a rod receiver and a shank extending distally from the head, in which the head has proximal and distal recesses therein. The cannulated shaft has a distal end that is configured to extend into the shank of the bone screw, and a proximal end that is configured to couple to a bone cement delivery system such that bone cement can be delivered through the cannulated shaft and into the shank of the bone screw. The guiding assembly includes a guiding sleeve having a distal end that is configured to couple to the proximal recess in the head of the bone screw, and a locking mechanism that is configured to couple to a proximal end of the guiding sleeve. The locking mechanism is configured to selectively lock the cannulated shaft and the guiding sleeve together to inhibit longitudinal movement of the cannulated shaft relative to the guiding sleeve. In some embodiments, a distal end of the locking mechanism can be configured to threadably couple to the proximal end of the retaining sleeve.

The locking mechanism can have a variety of configurations. For example, in some embodiments, the locking mechanism can include a release mechanism that can be configured to selectively engage a groove of the cannulated shaft. The locking mechanism can include a biasing element that can bias the release mechanism toward the groove of the cannulated shaft. The locking mechanism can include an annular body having a first portion, a second portion, and a lumen extending therebetween, in which the release mechanism is partially housed within the first portion of the annular body. The release mechanism can have a channel extending therethrough, in which the channel at least partially overlaps with the lumen of the annular body.

Methods for delivering bone cement to a bone screw are also provided. In one exemplary embedment, the method can include implanting a cannulated bone screw into bone, in which the bone screw has a head that is configured to couple to a rod receiver and a shank extending distally from the head. The head has proximal and distal recesses therein, in which the proximal recess is threadably coupled to a distal end of a retaining sleeve on an instrument. The method can also include inserting a distal end of a cannulated shaft through the retaining sleeve and into the shank of the bone screw, and injecting cement through the cannulated shaft and into the shank of the bone screw.

In some embodiments, implanting the cannulated bone screw in bone can include rotating the retaining sleeve relative to a screw drive assembly on the instrument to threadably engage the distal end of the retaining sleeve to the proximal recess of the bone screw, rotating the screw drive assembly to drive the bone screw into bone, and removing the screw drive assembly from the instrument while the retaining sleeve remains threadably engaged to the bone screw.

In some embodiments, the proximal end of the retaining sleeve can be coupled to a coupling assembly having a release mechanism, in which inserting the distal end of the cannulated shaft can cause the release mechanism to engage with a portion of the cannulated shaft upon the distal end reaching a predetermined insertion depth within the bone screw. In such embodiments, the method can include disengaging the release mechanism from the cannulated shaft to allow the cannulated shaft to be translated in a proximal direction and removed from the bone screw.

In some embodiments, the method can include, prior to injecting the cement, coupling a proximal end of the cannulated shaft to a bone cement delivery system. In other embodiments, the method can include, after injecting cement, coupling a rod receiver to the head of the bone screw.

BRIEF DESCRIPTION OF THE DRAWINGS

This invention will be more fully understood from the following detailed description taken in conjunction with the accompanying drawings, in which.

DETAILED DESCRIPTION

Figure 1:
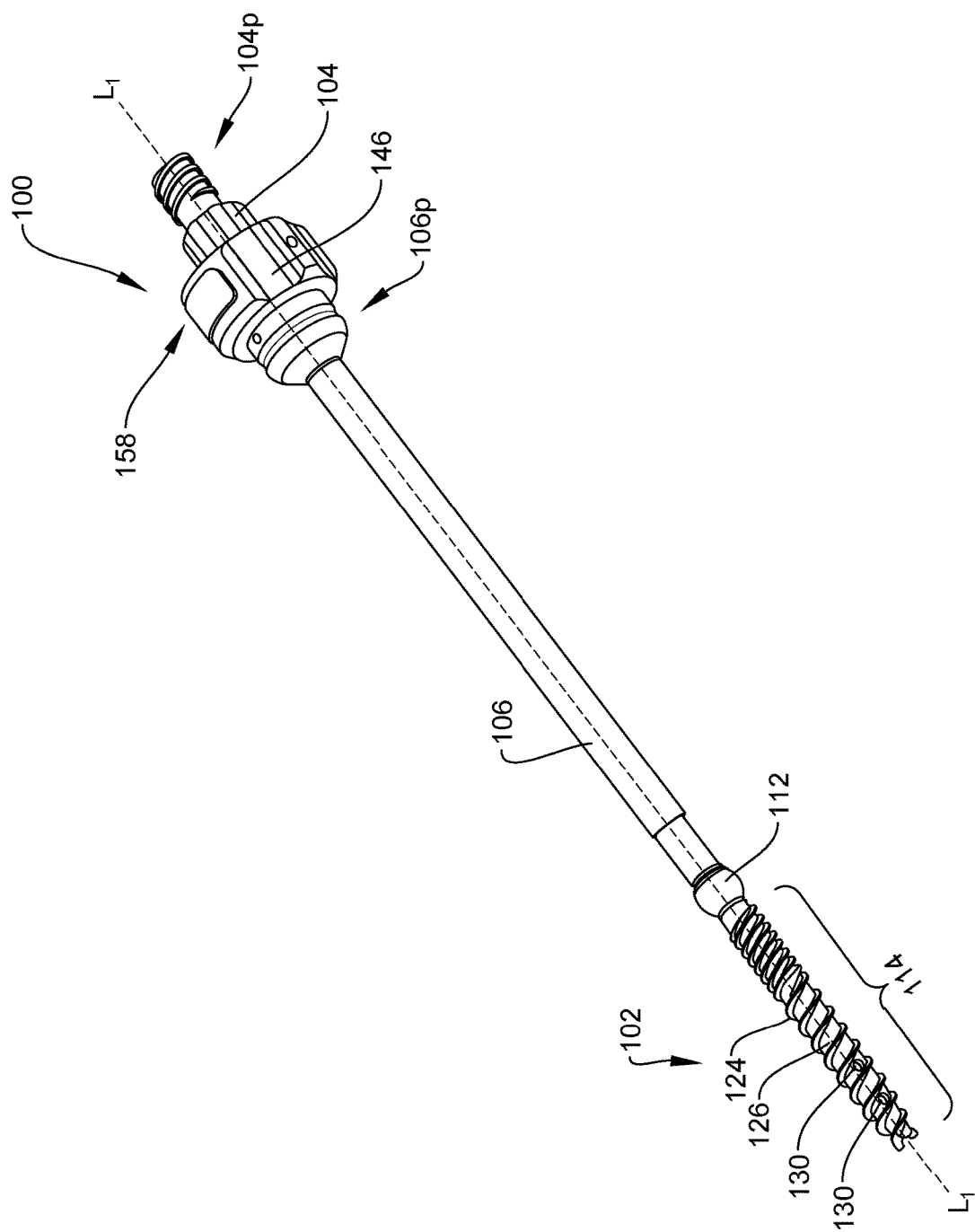
FIG. 1 is a perspective view of one embodiment of an instrument for delivering bone cement to screw.

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various surgical instruments and methods are provided for delivering bone cement to a bone screw. In some embodiments, the instruments and methods allow for driving a bone screw into bone, and thereafter maintaining a connection between the bone screw and the instrument. This connection can allow direct access to the implanted bone screw, e.g., for subsequent cement delivery, prior to attaching a rod receiver, e.g., a U-shaped rod receiver, to the head of the bone screw. Further, this connection can help control alignment with, and thus access to, the implanted bone screw. Cement delivery to the implanted bone screw can therefore be effected without the need to attach the rod receiver and dock a separate alignment guide thereto. As a result, this can provide intraoperative stability earlier on in the surgical procedure, streamline the procedure workflow, and reduce the number of surgical steps, and thus surgical time.

An exemplary instrument can include a variety of features to facilitate bone cement delivery to a bone screw, as described herein and illustrated in the drawings. However, a person skilled in the art will appreciate that the instruments can include only some of these features and/or can include a variety of other features known in the art. The instruments described herein are merely intended to represent certain exemplary embodiments.

FIGS. 1-5 illustrate one exemplary embodiment of an instrument 100 that is configured to deliver bone cement directly into a bone screw 102 prior to coupling a rod receiver (not shown) thereto. The illustrated instrument 100 generally includes a cannulated shaft 104, a retaining sleeve 106, also referred to herein as a guiding sleeve, disposed around a portion of the cannulated shaft 104, and a coupling assembly 108, also referred to herein as a locking mechanism. The guiding sleeve and the locking mechanism are collectively referred to herein as a guiding assembly. For purposes of simplicity, certain components of the instrument 100 are not illustrated in FIGS. 1-3B.

While the bone screw 102 can have a variety of configurations, the bone screw 102, as shown in FIGS. 1-3B and 5, has a head 112 and a shank 114 extending distally from the head 112. The head 112 can have a variety of shapes and sizes. As shown, the head 112 is generally in the shape of a truncated sphere and includes proximal and distal recesses 116, 118 defined therein. The proximal recess 116 can be substantially cylindrical with internal threads 120 formed therein for engaging a corresponding threaded portion of the retaining sleeve 106, as discussed below. The distal recess 118 can be shaped to non-rotatably engage a distal tip of a driver shaft (not shown), as discussed below. For example, the distal recess 118 can be in the form of a female mating feature (e.g., a hex recess) and the distal tip of the driver shaft can be in the form of a male mating feature (e.g., a hex protrusion) such that the distal tip of the driver shaft can mate to the bone screw 102. In this illustrated embodiment, the head 112 includes a threaded proximal recess 116 and a non-threaded distal recess 118.

Figure 6:
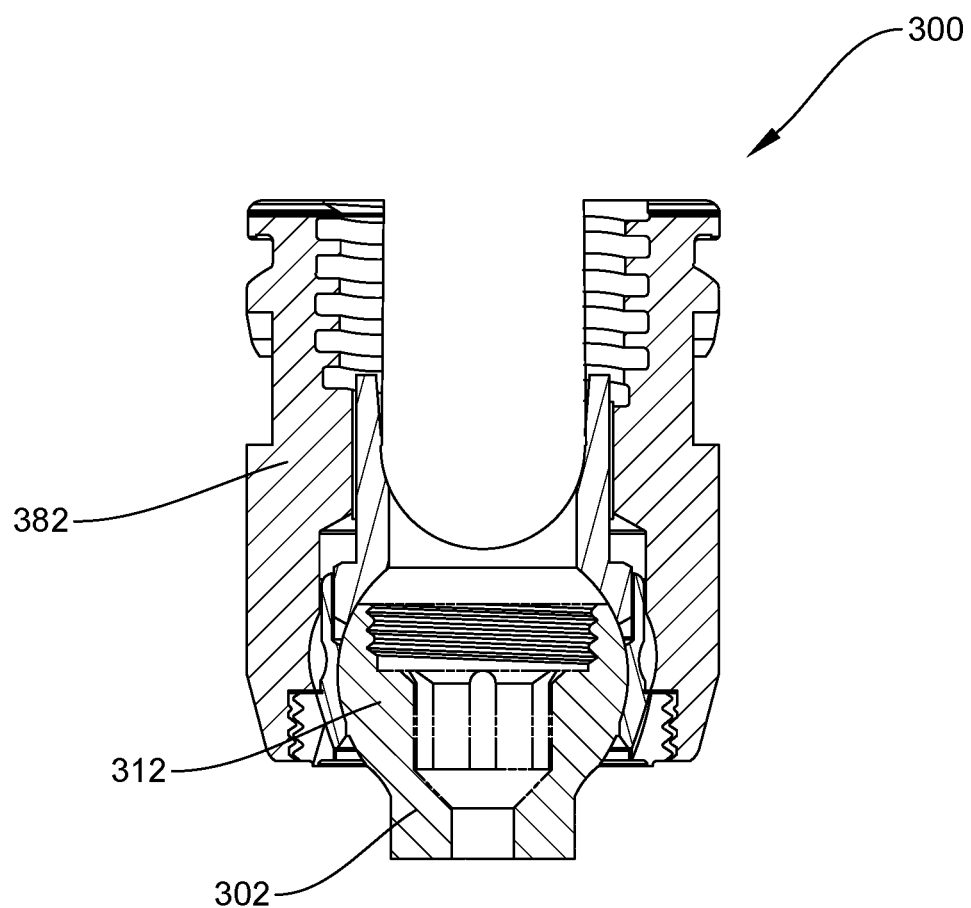
FIG. 6 is a cross-sectional view of an embodiment of a bone screw assembly.
Figure 7:
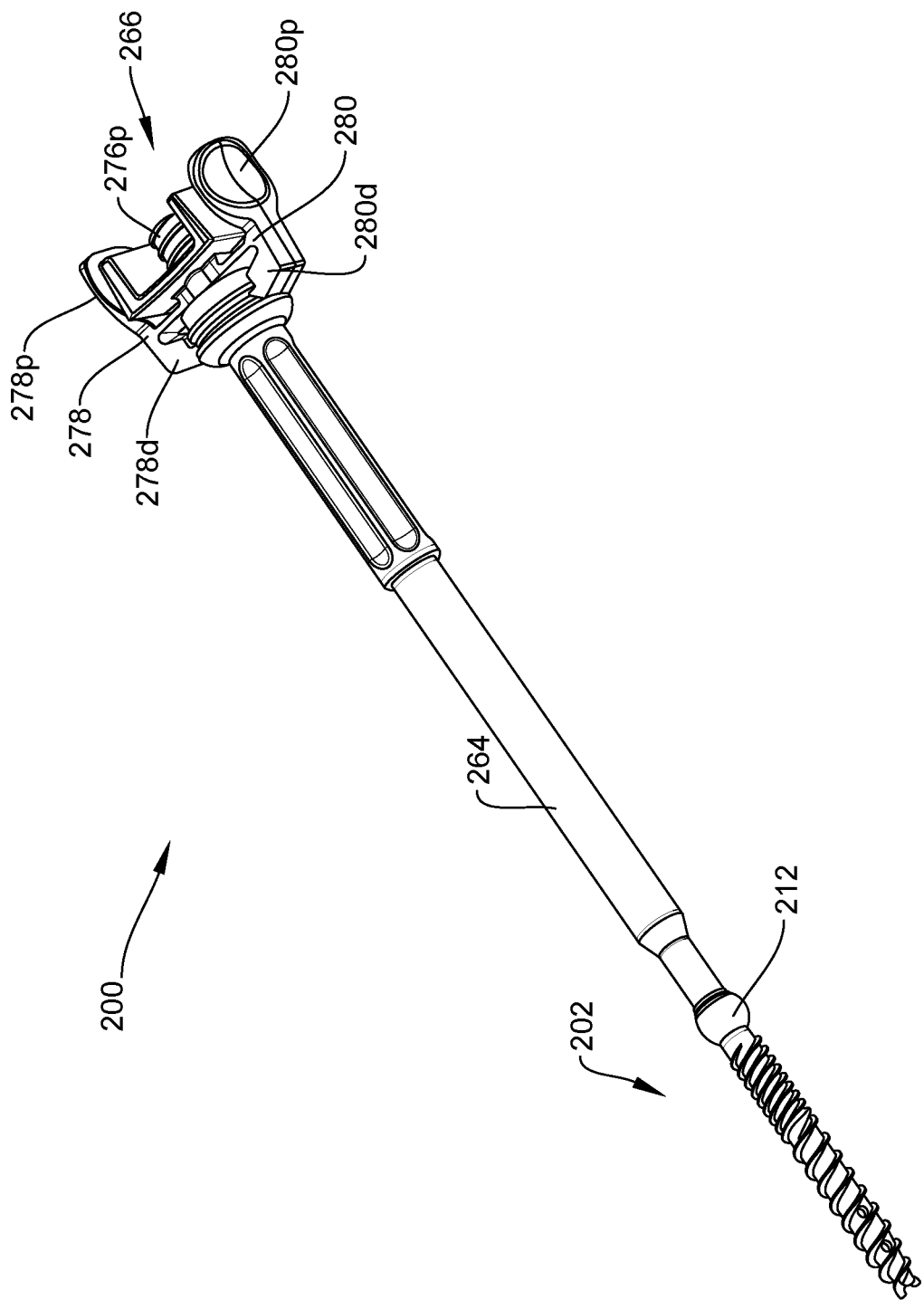
FIG. 7 is a perspective view of another embodiment of an instrument for delivering bone cement to a bone screw.
Figure 8:
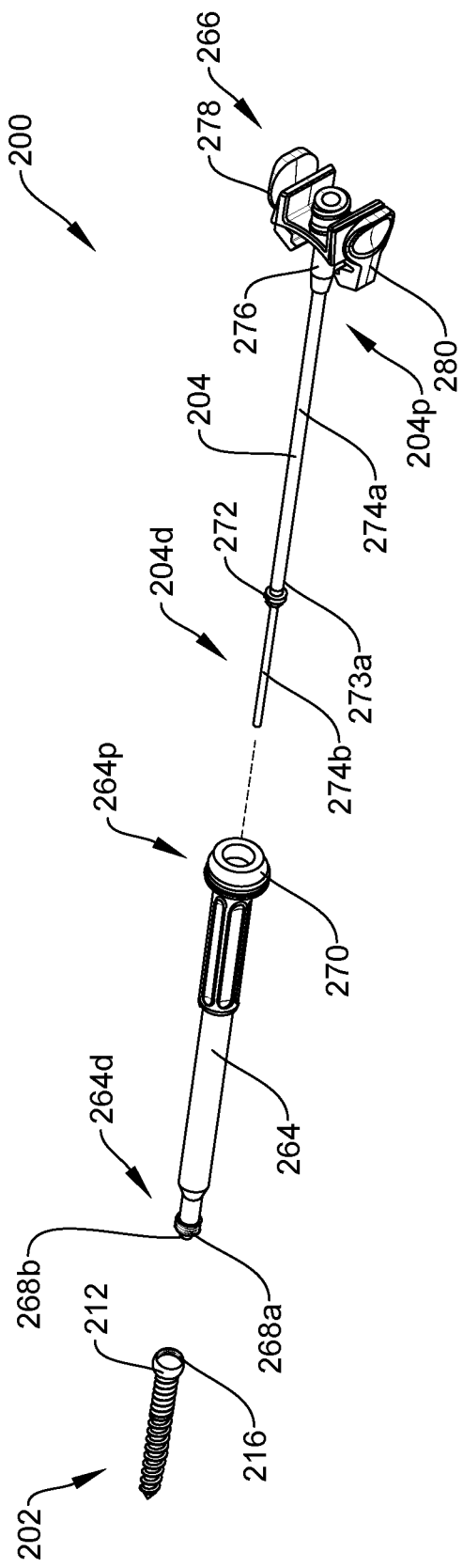
FIG. 8 is a partial exploded view of the instrument of FIG. 7.
Figure 9A:
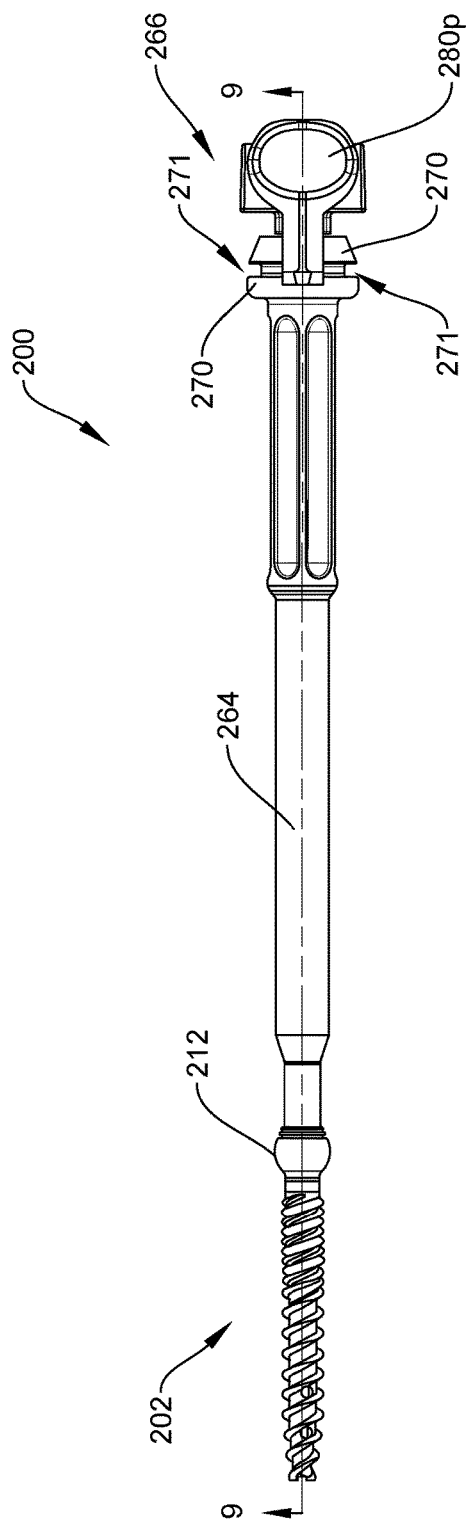
FIG. 9A is a side view of the instrument of FIG. 8.
Figure 9B:
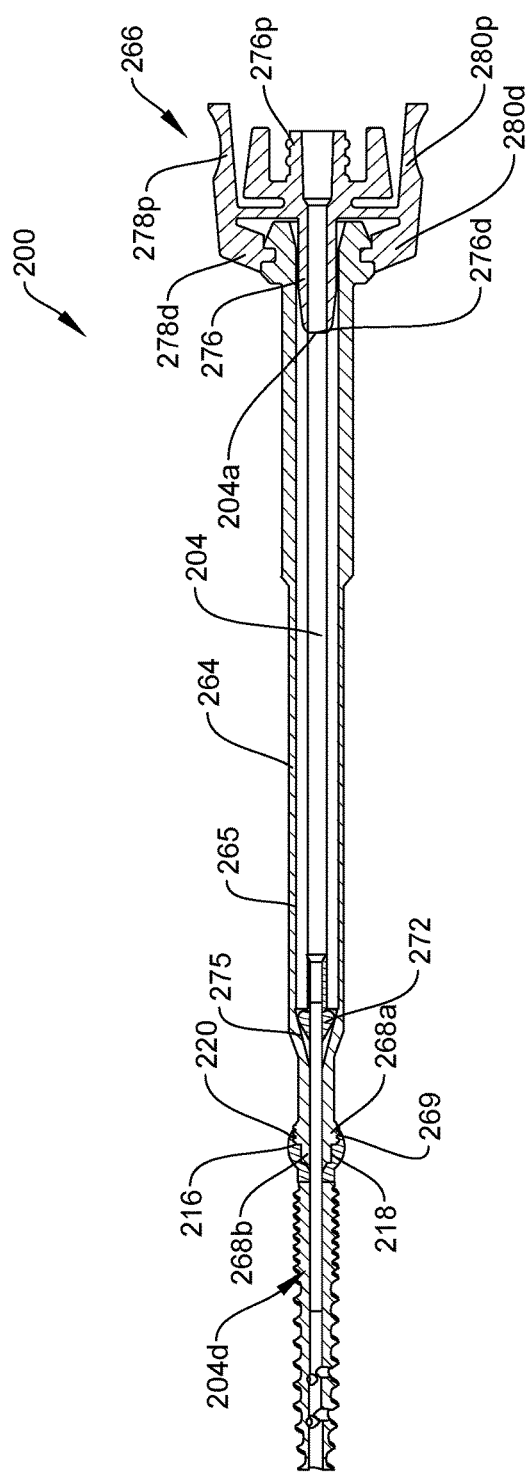
FIG. 9B is a cross-sectional view of the instrument of FIG. 9A taken at 9-9.

Further, the head 112 is configured to be coupled to a rod receiver. In this way, once cement is delivered to the bone screw 102 and the instrument 100 is removed therefrom, as will be discussed in more detail below, the head 112 of the bone screw 102 is exposed for subsequent attachment to a rod receiver to form a bone screw assembly. An exemplary bone screw assembly 300 is illustrated in FIG. 6, in which a rod receiver 382 is attached to a head 312 of a cannulated bone screw 302. While the rod-receiver 382 can have a variety of configurations, in this illustrated embodiment, the rod receiver 382 is substantially U-shaped. In other embodiments, the rod receiver 382 can have other suitable configurations, e.g., a rod receiver having an enclosed thru-hole or a substantially C-shaped rod receiver. In some embodiments, the bone screw assembly is polyaxial. A person skilled in the art will appreciate that the head of the cannulated bone screw can have other suitable shapes and sizes. Exemplary embodiments of suitable bone screws and bone screw assemblies are described in more detail in U.S. Patent Publication Nos. 2018/0014858 and 2018/0014862, each of which is hereby incorporated by reference in its entirety.

The shank 114 of the bone screw 102 can have a variety of shapes and sizes. As shown, the shank 114 is in the form of an elongated body with threads 124 formed on at least a portion of its exterior surface 126. The illustrated shank 114 includes a lumen 128 extending entirely therethrough. In other embodiments, the lumen 128 can extend through only a portion of the shank 114. The lumen 128 is in fluid communication with the proximal and distal recesses 116, 118 of the head 112. As a result, a distal end 104d of the cannulated shaft 104 can be inserted through the head 112 of the bone screw 102 and into at least a portion of the shank 114, as shown in FIGS. 1-3B and 5, to allow bone cement to be delivered therethrough and into the bone screw 102. The shank 114 can also include at least one fenestration 130, e.g., aperture, extending outward from the lumen 128 to the exterior surface 126 of the shank 114. At least one fenestration 130 is configured to direct bone cement that is injected into the bone screw 102 towards bone that is proximate to the bone screw 102, e.g., when the bone screw 102 is implanted. The position and number of fenestrations within the shank 114 of the bone screw 102 can vary.

As shown in FIGS. 1-3B and 5, the retaining sleeve 106 is coupled to the head 112 of the bone screw 102. While the retaining sleeve 106 can have a variety of configurations, in this illustrated embodiment, the retaining sleeve 106 has an elongated, cylindrical shape that extends from a proximal end 106p to a distal end 106d. The distal end 106d of the retaining sleeve 106 is configured to couple to the head 112 of the bone screw 102 to deliver bone cement subsequently thereto. The retaining sleeve 106 also includes a lumen 134 that is configured to receive components, e.g., a driver shaft for driving the bone screw 102 into bone, the cannulated shaft 104, as shown in FIGS. 1-3B and 4. In this illustrated embodiment, the lumen 134 extends from the proximal end 106p to the distal end 106d of the retaining sleeve 106 along the longitudinal axis (Li) of the instrument. As a result, the retaining sleeve 106 can function as a guide for the cannulated shaft 104, which is inserted through the retaining sleeve 106 and into the coupled bone screw 102, as shown in FIGS. 1-3B and 5. This allows cement to be delivered into the bone screw 102 prior to attaching a rod receiver to the head 112 of the bone screw 102.

The distal end 106d of the retaining sleeve 106, as shown, includes threads 132 that are threadably engaged with the corresponding internal threads 120 of the proximal recess 116 of the head 112 of the bone screw 102. As such, the retaining sleeve 106 is threadably coupled to the bone screw 102 itself. A person skilled in the art will appreciate that the retaining sleeve 106 and the bone screw 102 can be coupled to each other using other coupling mechanisms. For example, in other embodiments, the head of the bone screw can have an outer surface that is configured to couple to an inner surface of the retaining sleeve via a pressure fit (e.g. collet mechanism).

Further, as shown in FIGS. 1-4, the proximal end 106p of the retaining sleeve 106 is attached to the coupling assembly 108. The proximal end 106p of the retaining sleeve 106 includes a proximal cavity 136 having internal threads 138 that are threadably engaged with a threaded portion of the coupling assembly 108. The proximal end 106p also includes first and second channels 135, 137 that extend laterally through a wall 109 of the retaining sleeve 106 (e.g., orthogonally to the longitudinal axis ($L_I$) of the instrument). The first and second channels 135, 137 are in communication with corresponding third and fourth channels 139, 140 that extend laterally through a wall 110 of the coupling assembly 108 (e.g., orthogonally to the longitudinal axis ($L_I$) of the instrument). In particular, the first and third channels 135, 139 are engaged via a first set pin 143 and the second and fourth channels 137, 140 are engaged via a second set pin 144. In this way, during use, the retaining sleeve 106 and the coupling assembly 108 are prevented from unthreading from each other, and thus from decoupling. A person skilled in the art will appreciate that the retaining sleeve 106 and the coupling assembly 108 can be coupled to each other using other coupling mechanisms, or that the retaining sleeve 106 and the coupling assembly 108 may be formed together from a single continuous profile.

Figure 2:
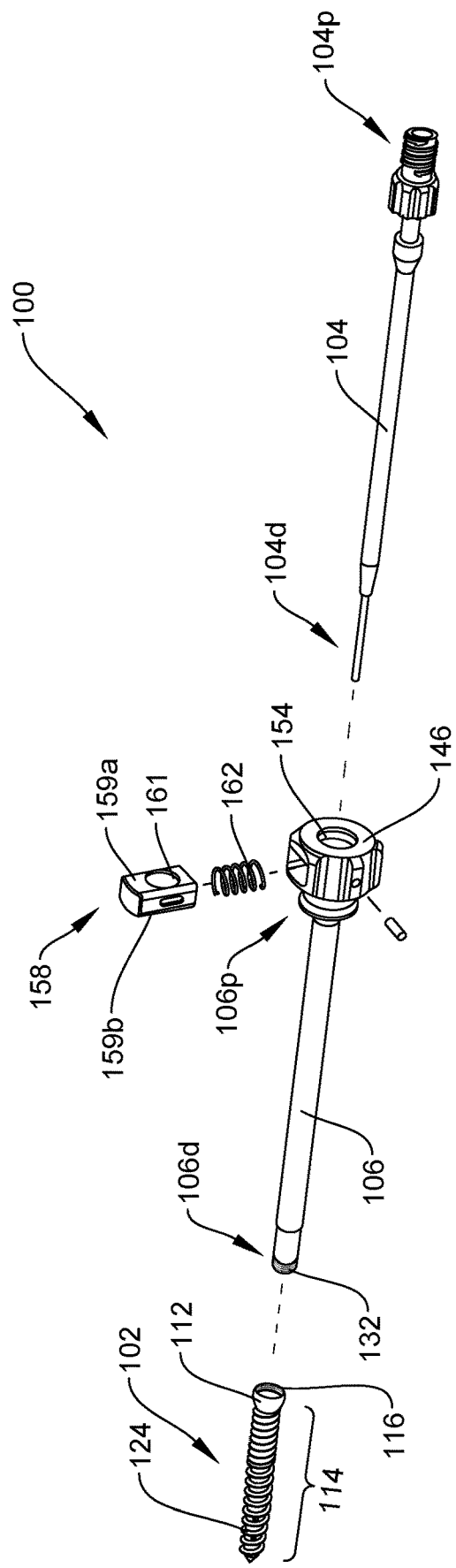
FIG. 2 is a partial exploded view of the instrument of FIG. 1.
Figure 3A:
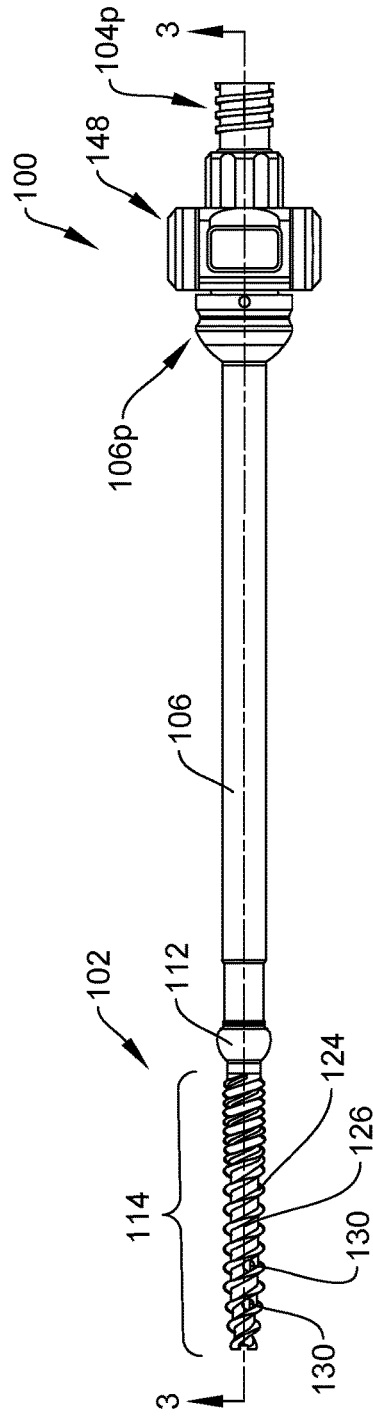
FIG. 3A is a top view of the instrument of FIG. 1.
Figure 3B:
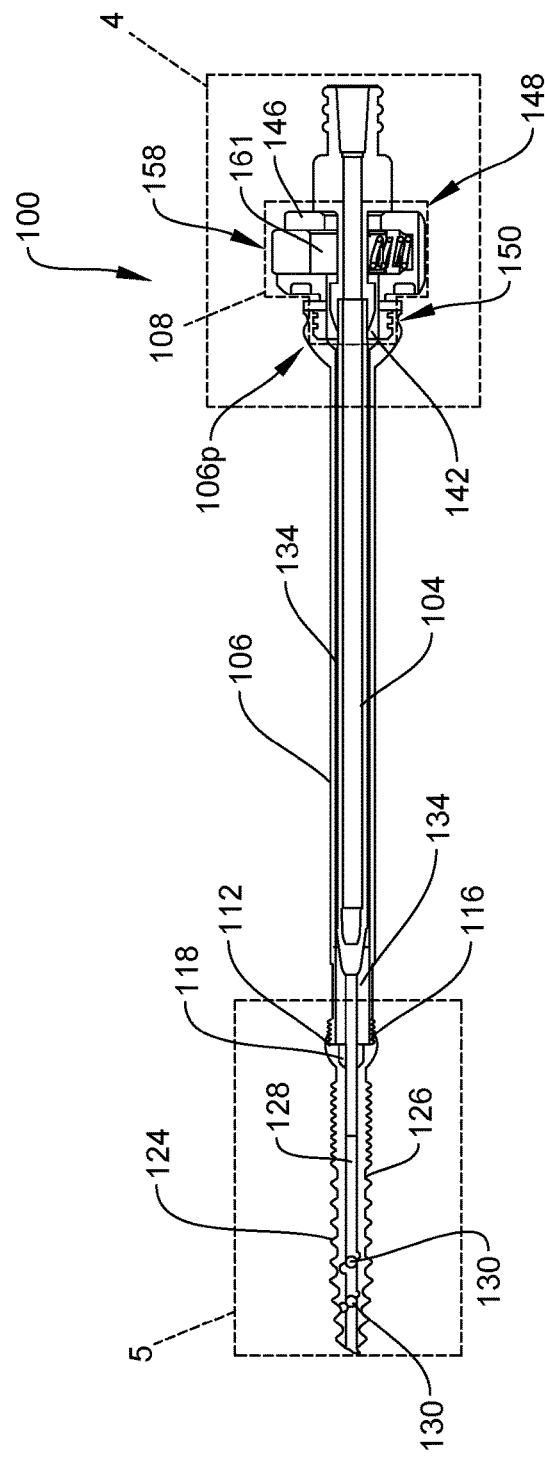
FIG. 3B is a cross-sectional view of the instrument of FIG. 3A taken at 3-3.
Figure 4:
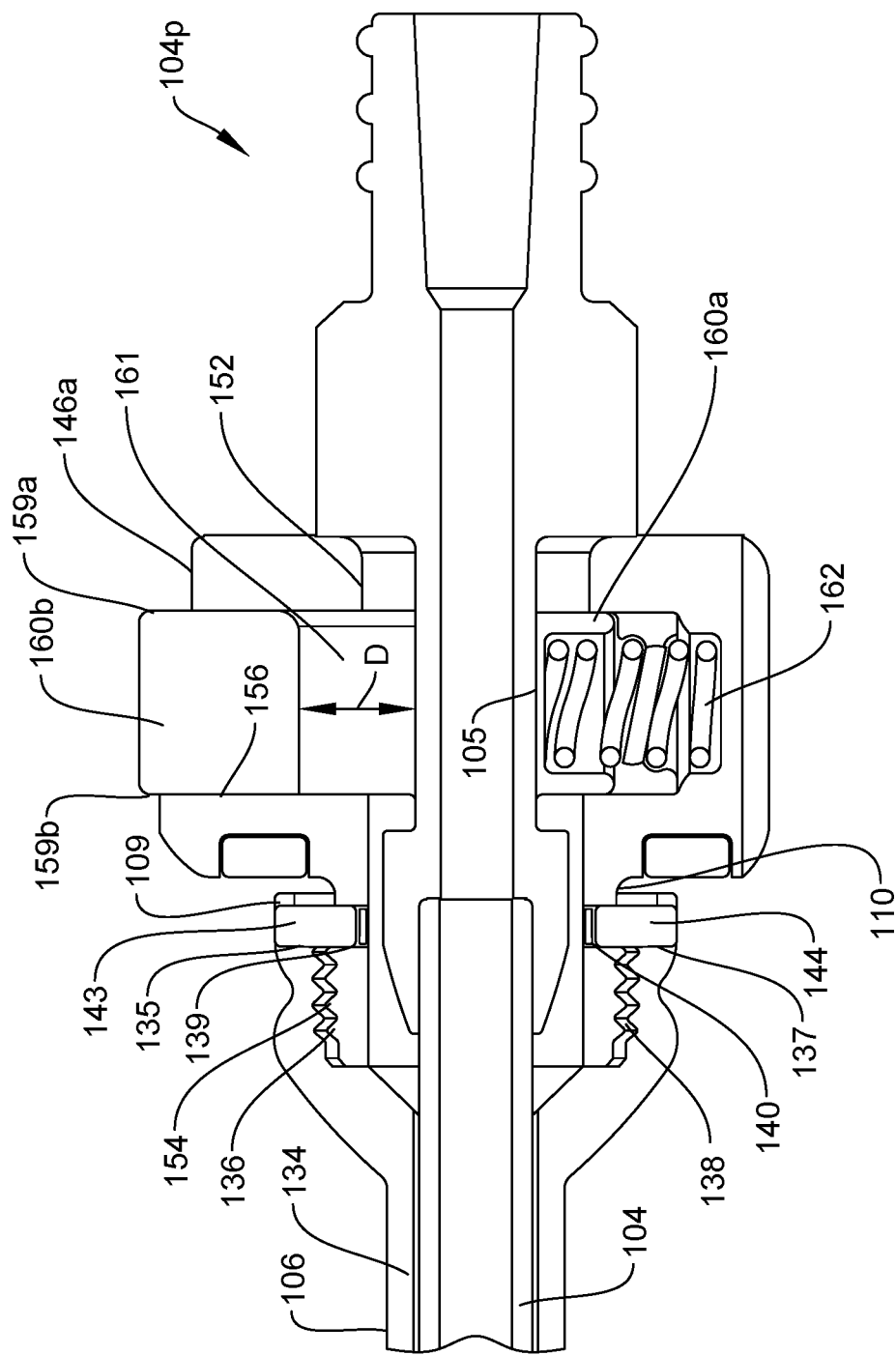
FIG. 4 is a magnified cross-sectional view of a portion of the instrument of FIG. 3B taken at 4.
Figure 5:
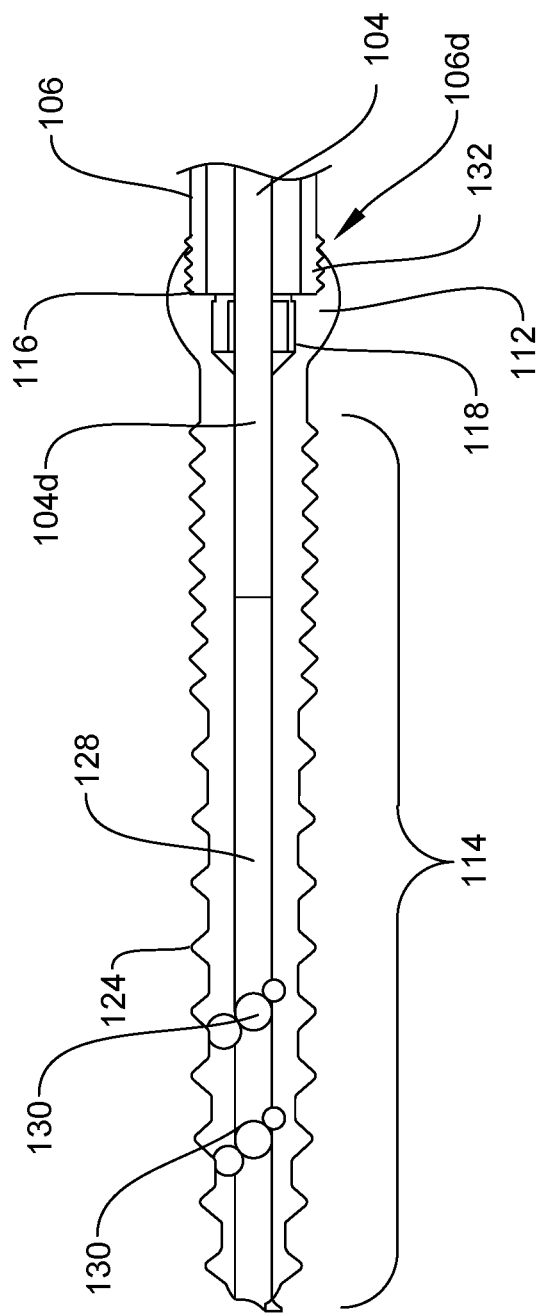
FIG. 5 is a magnified cross-sectional view of a portion of the instrument of FIG. 3B taken at 5.

The coupling assembly can have a variety of configurations. The illustrated coupling assembly 108 includes an elongated annular body 146 having a proximal end 148, a distal end 150, and a lumen 152 extending therebetween, as shown in FIGS. 1-4. The lumen 152 extends along the longitudinal axis of the instrument (Li) and is in communication with the lumen 134 of the retaining sleeve 106. As shown in FIGS. 3B and 4, the distal end 150 includes outer threads 154 that are threadably engaged to the internal threads 138 of the proximal cavity 136 of the retaining sleeve 106, and the third and fourth channels 139, 140 that are engaged with the first and second channels 135, 137 of the proximal cavity 136 via corresponding set pins 143, 144. The proximal end 148 of the annular body 146 includes an aperture 156 extending radially outward from the lumen 152 and through an outer surface 146a of the annular body 146.

The coupling assembly can also include a release mechanism, e.g., a release button. As shown, the coupling assembly 108 includes a release button 158 that is partially housed within the proximal end 148 of the annular body 146. While the release button 158 can have a variety of configurations, in this illustrated embodiment, the release button 158 is substantially rectangular in shape and includes a first portion 160a and a second portion 160b. Further, a channel 161 extends from a first surface 159a to a second surface 159b of the release button 158. As shown in FIGS. 3B and 4, the channel 161 at least partially overlaps with the lumen 152 of the annular body 146. As a result, the coupling assembly 108 is disposed around a portion of the cannulated shaft 104, as shown in FIGS. 1 and 3A-4.

Further, the release button 158 is coupled to a biasing element 162 that is configured to bias the first portion 160a of the release button 158 toward the lumen 142 of the annular body 146 and the second portion 160b of the release button 158 away from the lumen 142 of the annular body. While the biasing element 162 can have a variety of configurations, the biasing element 162, as shown in FIGS. 2, 3B and 4, is in the form of a helical spring.

The coupling assembly 108 is configured to selectively couple components, e.g., a driver shaft of a screw drive assembly and the cannulated shaft 104, as shown in FIGS. 1 and 3A-4, to the retaining sleeve 106. In use, the bone screw 102 can be inserted into bone using a screw drive assembly (not shown) that is releasably coupled to the retaining sleeve 106 via the coupling assembly 108. The screw drive assembly and the retaining sleeve 106 are collectively referred to herein as a screw inserter instrument. The screw drive assembly can include a handle and a driver shaft that is coupled to the handle. The driver shaft can be inserted through the retaining sleeve 106 to engage the distal recess 118 of the bone screw 102 and drive the bone screw 102 into bone. As such, the bone screw 102 can be coupled to the screw inserter instrument, for example, by inserting the distal tip of the driver shaft into the distal recess 118 of the head 112 of the bone screw 102 and threadably engaging the distal end 106d of the retaining sleeve 106 to the proximal recess 116 of the head 112 of bone screw 102. The bone screw 102 can be driven into bone by rotating the screw drive assembly relative to the retaining sleeve 106. Additional details on the screw drive assembly and other exemplary embodiments of screw inserter instruments can be found, for example, in U.S. patent application Ser. Nos. 16/440,602 and 16/440,618, filed on Jun. 13, 2019, entitled "Screw Inserter Instruments and Methods," each of which is incorporated by reference herein in its entirety.

Once the bone screw 102 is inserted into bone, the screw drive assembly is decoupled (e.g., by depressing the second portion 160b of the release button 158 of the coupling assembly 108), and removed from the retaining sleeve 106, and thus, the bone screw 102, while the retaining sleeve 106 remains threadably engaged to the bone screw 102. As a result, once the screw drive assembly is removed, the cannulated shaft 104 can be inserted into and coupled to the retaining sleeve 106 via the coupling assembly 108, as shown in FIGS. 1 and 3A-4. In this way, the retaining sleeve 106 can function as an alignment guide that provides access to the bone screw after its insertion such that bone cement can be injected therein. This avoids the need to couple, e.g., thread, a separate alignment guide to the bone screw 102 to guide the cannulated shaft 104, and thus bone cement, into the bone screw 102.

While the cannulated shaft 104 can have a variety of configurations, the cannulated shaft 104, as shown in FIGS. 1-3B, is in the form of a generally elongated hollow tube that extends from a proximal end 104p to a distal end 104d of the cannulated shaft 104. The distal end 104d extends into a portion of the bone screw 102. The proximal end 104p of the cannulated shaft 104 is configured to be coupled (e.g., threadably coupled) to a bone cement delivery system (not shown) such that bone cement can be delivered from the system, through the cannulated shaft 104, and into the bone screw 102. As will be appreciated by a person skilled in the art, any bone cement delivery system can be configured to couple to the cannulated shaft 104 to deliver bone cement therethrough. Exemplary embodiments of bone cement delivery systems can be found in U.S. Pat. Nos. 7,097,648, 8,360,629, 8,415,407, and 9,381,024, and U.S. Patent Publication Nos. 2006/0264967, 2007/0032567, 2008/0228192, and 2010/0114174, each of which is hereby incorporated by reference in its entirety.

As shown in FIGS. 3B and 4, the cannulated shaft 104 is coupled to the retaining sleeve 106 via the coupling assembly 108. In this illustrated embodiment, the release button 158 engages with a groove 105 of the cannulated shaft 104 adjacent to the proximal end 104p of the cannulated shaft 104. In particular, the first portion 160a is configured to engage the groove 105, and the second portion 160b is configured to be spaced from the groove 105 at a distance (D). This distance, as described in more detail below, can allow the second portion 160b to be selectively depressed towards the groove 105 so as to move the first portion 160a away from the groove 105, thereby decoupling the cannulated shaft 104 and the retaining sleeve 106. As shown in FIG. 3B, the release button 158 is engaged to the cannulated shaft 104 via the biasing element 162 in an extended configuration. As a result, the first portion 160a of the release button 158 is biased toward the groove 105 and the second portion 160b of the release button 158 is biased away from the groove 105 at distance (D).

In use, the cannulated shaft 104 is inserted into the retaining sleeve 106 until the first portion 160a of the release button 158 slides into contact with and engages the groove 105 of the cannulated shaft 104. In this way, the distal end 104d of the cannulated shaft 104 is inserted into the bone screw 102 at a predetermined insertion depth. Once bone cement is delivered through the cannulated shaft 104 and into the bone screw 102 (e.g., when a desired amount of bone cement is injected into the bone screw), the cannulated shaft 104 can be removed from the retaining sleeve 106. To remove the cannulated shaft 104 from the retaining sleeve 106, the release button 158 can be actuated to cause the first portion 160a of the release button 158 to move away from, and thus disengage, the groove 105. For example, a user can actuate the release button 158 by applying sufficient force to the second portion 160b thereof such that the second portion 160b moves towards the groove 105. This causes the first portion 160a of the release button 158 to shift away from the groove 105 and the biasing element 162 to move into a compressed configuration. As a result, the first portion 160a of the release button 158 disengages the groove 105 of the cannulated shaft 104, thereby allowing the cannulated shaft 104 to be slidably removed (e.g., translated in a proximal direction) from at least the bone screw 102.

FIGS. 7-9B illustrate another embodiment of an instrument 200 that is configured to deliver bone cement to a bone screw 202. Aside from the differences described in detail below, the instrument 200 is similar to instrument 100 shown in FIGS. 1-4 and therefore common elements are not further described in detail herein. Further, for purposes of simplicity, certain components of the instrument 200 are not illustrated in FIGS. 7-9B.

In this illustrated embodiment, the instrument 200 includes an alignment guide 264, a cannulated shaft 204 extending therethrough, and a coupling element 266 that is configured to releasably couple the cannulated shaft 204 to the alignment guide 264.

Once the bone screw 202 is inserted into bone, the alignment guide 264 can be coupled to the head 212 of the bone screw 202. The alignment guide 264 can have a variety of configurations. In this illustrated embodiment, the alignment guide 264 is in the form of a generally elongated hollow tube that extends from a proximal end 264p to a distal end 264d. The distal end 264d includes a threaded portion 268a and a non-threaded portion 268b extending distally therefrom. The threaded portion 268a includes threads 269 that threadably engage with the corresponding internal threads 220 of the proximal recess 216 of the head 212 of the bone screw 202, as shown in FIGS. 7-9B. The non-threaded portion 268b is formed within the distal recess 218 of the head 212 of the bone screw 202. Further, the proximal end 264p of the alignment guide 264 includes an annular collar 270 having a connection feature 271 that is configured to engage with the coupling element 266, as shown in FIGS. 7-9B. In this illustrated embodiment, the connection feature 271 is an annular groove or notch. In other embodiments, the connection feature 271 can have other configurations.

While the cannulated shaft 204 can have a variety of configurations, the cannulated shaft 204, as shown, is in the form of a generally elongated hollow tube that extends from a proximal end 204p to a distal end 204d. The distal end 204d extends into a portion of the bone screw 202. Further, the cannulated shaft 204 includes a ferrule 272 that extends radially outward from an outer surface 273a of the cannulated shaft 204. The ferrule 272 is interposed between a first segment 274a and a second segment 274b of the cannulated shaft 204. The ferrule 272 can have a variety of shapes and sizes. In this illustrated embodiment, the ferrule 272 has a substantially conical shaped configuration. The ferrule 272 is configured to contact a tapered portion 275 of the inner surface 265 of the alignment guide 264 so as to limit the insertion depth of the distal end 204d of the cannulated shaft 204 into the bone screw 202. As a result, this contact between the ferrule 272 and the tapered portion 275 can prevent a user from inserting the distal end 204d of the cannulated shaft 204 too far into, or entirely through, the bone screw 202.

As shown, the coupling element 266 is fixedly attached to the cannulated shaft 204. The coupling element 266 can have a variety of configurations. In this illustrated embodiment, the coupling element 266 includes a hollow tubular base member 276 with two spaced-apart arms 278, 280 extending radially outward therefrom. The distal end 276d of the tubular base member 276 is fixedly coupled to the proximal-most end 204a of the cannulated shaft 204. The proximal end 276p of the tubular base member 276 is configured to be coupled (e.g., threadably coupled) to a bone cement delivery system (not shown) such that bone cement can be delivered from the system, through the tubular base member 276 and cannulated shaft 204, and into the bone screw 202. As will be appreciated by a person skilled in the art, any bone cement delivery system can be configured to couple to the tubular base member 276 to deliver bone cement therethrough. Exemplary embodiments of bone cement delivery systems can be found in previously mentioned U.S. Pat. Nos. 7,097,648, 8,360,629, 8,415,407, and 9,381,024, and U.S. Patent Publication Nos. 2006/0264967, 2007/0032567, 2008/0228192, and 2010/0114174, each of which is hereby incorporated by reference in its entirety.

Further, as shown in FIGS. 7-9B, the cannulated shaft 204 is releasably coupled to the alignment guide 264 via the two spaced-apart arms 278, 280 of the coupling element 266. In particular, the distal end 278d, 280d of each arm 278, 280 engages with the connection feature 271 of the alignment guide 264. In use, the distal ends 278d, 280d of the arms 278, 280 can either slide or snap into engagement with the connection feature 271. To decouple the cannulated shaft 204 from the alignment guide 264, the proximal ends 278p, 280p of the arms 278, 280 can be compressed together to cause the distal ends 278d, 280d to move away from each other and out of engagement with connection feature 271. Once the distal ends 278d, 280d are disengaged, the cannulated shaft 204 can be removed.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning/replacement, and reassembly. Use of such techniques, and the resulting reconditioned instrument, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, instruments, and methods, such dimensions are not intended to limit the types of shapes that can be used in conjunction with such systems, instruments, and methods. A person skilled in the art will recognize that an equivalent to such linear and circular dimensions can easily be determined for any geometric shape. Sizes and shapes of the systems and instruments, and the components thereof, can depend at least on the anatomy of the subject in which the systems and instruments will be used, the size and shape of components with which the systems and instruments will be used, and the methods and procedures in which the systems and instruments will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that there are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A system, comprising:
a cannulated bone screw having a head that is configured to be received within a rod receiver, and a shank extending distally from the head and configured to extend distally from the rod receiver, the head having proximal and distal recesses therein; and
an instrument for delivering bone cement to the cannulated bone screw, the instrument comprising
a cannulated shaft having a distal end configured to extend into the shank of the cannulated bone screw, and a proximal end configured to couple to a bone cement delivery system, and
a retaining sleeve disposed around at least a portion of the cannulated shaft, the retaining sleeve having a distal end that is configured to couple to the proximal recess in the head of the bone screw.

2. The system of claim 1, wherein the instrument further comprises a coupling assembly that is configured to selectively couple the cannulated shaft to the retaining sleeve to prevent axial translation of the cannulated shaft relative to the retaining sleeve.

3. The system of claim 2, wherein the coupling assembly includes a release mechanism that is configured to selectively disengage the cannulated shaft from the retaining sleeve.

4. The system of claim 3, wherein the coupling assembly includes a biasing element that biases the release mechanism toward a groove of the cannulated shaft.

5. The system of claim 3, wherein the release mechanism has a channel extending therethrough, and wherein the channel at least partially overlaps with a lumen that extends through an annular body such that the coupling assembly is disposed around a portion of the cannulated shaft.

6. The system of claim 2, wherein the coupling assembly is coupled to the proximal end of the retaining sleeve.

7. The system of claim 6, wherein a distal end of the coupling assembly is threadably coupled to the proximal end of the retaining sleeve.

8. The system of claim 1, wherein the proximal recess of the cannulated bone screw is threaded, and wherein the distal end of the retaining sleeve is threadably coupled to the proximal recess.

9. The system of claim 1, wherein the instrument further comprises a coupling assembly that is configured to selectively engage a groove of the cannulated shaft, and wherein the groove is associated with a predetermined insertion depth of the distal end of the cannulated shaft into the cannulated bone screw.

10. The system of claim 1, wherein the instrument further comprises a coupling assembly that is configured to selectively couple the retaining sleeve to a drive shaft of a screw driver assembly to implant the cannulated bone screw into bone.

11. A system, comprising:
a cannulated bone screw having a head that is configured to couple to a rod receiver and a shank extending distally from the head, the head having proximal and distal recesses therein; and
an instrument for delivering bone cement to the cannulated bone screw, the instrument comprising
a cannulated shaft having a distal end that is configured to extend into the shank of the bone screw, and a proximal end that is configured to couple to a bone cement delivery system such that bone cement can be delivered through the cannulated shaft and into the shank of the bone screw, and
a guiding assembly that is partially disposed around the cannulated shaft and including a guiding sleeve having a distal end that is configured to couple to the proximal recess in the head of the bone screw, and a locking mechanism that is configured to couple to a proximal end of the guiding sleeve, the locking mechanism being configured to selectively lock the cannulated shaft and the guiding sleeve together to inhibit longitudinal movement of the cannulated shaft relative to the guiding sleeve.

12. The system of claim 11, wherein a distal end of the locking mechanism is configured to threadably couple to the proximal end of the guiding sleeve.

13. The system of claim 11, wherein the locking mechanism includes a release mechanism that is configured to selectively engage a groove of the cannulated shaft.

14. The system of claim 13, wherein the locking mechanism includes a biasing element that biases the release mechanism toward the groove of the cannulated shaft.

15. The system of claim 13, wherein the locking mechanism further comprises an annular body having a first portion, a second portion, and a lumen extending therebetween, and wherein the release mechanism is partially housed within the first portion of the annular body.

16. The system of claim 15, wherein the release mechanism has a channel extending therethrough, and wherein the channel at least partially overlaps with the lumen of the annular body.

17. The system of claim 11, wherein the locking mechanism comprises a releasing mechanism that is configured to selectively engage a groove of the cannulated shaft, and wherein the groove is associated with a predetermined insertion depth of a distal end of the cannulated shaft into the cannulated bone screw.

18. The system of claim 11, wherein the locking mechanism includes a release button that is configured to selectively disengage the cannulated shaft from the guiding sleeve.

19. The system of claim 11, wherein the locking mechanism is further configured to selectively lock the guide sleeve to a drive shaft of a screw driver assembly to implant the cannulated bone screw into bone.

20. The system of claim 11, wherein the proximal recess of the cannulated bone screw is threaded, and wherein the distal end of the guiding sleeve is configured to threadably couple to the proximal recess.

* * * * *